United States Patent [19]
Prud'Homme et al.

[11] Patent Number: 4,656,301
[45] Date of Patent: Apr. 7, 1987

[54] DIRECT CATALYTIC SYNTHESIS OF DIMETHYLDICHLOROSILANE FROM METHYL CHLORIDE AND SILICON

[75] Inventors: Christian Prud'Homme, Lyons; Gerard Simon, Roussillon, both of France

[73] Assignee: Rhone-Poulenc Specialites Chimiques, Courbevoie, France

[21] Appl. No.: 655,729

[22] Filed: Sep. 28, 1984

[30] Foreign Application Priority Data

Sep. 28, 1983 [FR] France ................. 83 15401

[51] Int. Cl.$^4$ ............................. C07F 7/16
[52] U.S. Cl. .................... 556/472; 502/244
[58] Field of Search ............ 556/472; 502/244

[56] References Cited

U.S. PATENT DOCUMENTS

| | | | |
|---|---|---|---|
| 2,380,995 | 8/1945 | Roehow | 556/472 |
| 2,889,350 | 6/1959 | Horny et al. | 556/472 |
| 2,917,529 | 12/1959 | Drysdale | 556/472 |
| 3,155,698 | 11/1969 | Nitzsche et al. | 556/472 |
| 3,555,064 | 11/1971 | Turetskaya et al. | 556/472 |
| 4,170,570 | 10/1979 | Zagata et al. | 502/244 X |

FOREIGN PATENT DOCUMENTS

| | | | |
|---|---|---|---|
| 0151336 | 3/1962 | U.S.S.R. | 556/472 |
| 0249387 | 8/1969 | U.S.S.R. | 556/472 |
| 0352903 | 9/1972 | U.S.S.R. | 556/472 |
| 0810707 | 3/1981 | U.S.S.R. | 556/472 |

*Primary Examiner*—Paul F. Shaver
*Attorney, Agent, or Firm*—Burns, Doane, Swecker & Mathis

[57] ABSTRACT

Dimethyldichlorosilane is directly prepared from methyl chloride and silicon, in high productivity, selectivity and degree of silicon conversion, by reacting methyl chloride with a solid contact mass comprising silicon and a catalytically effective amount of a catalyst which includes (1) elemental copper or a copper compound, (2) from about 30 to 1,000 ppm (calculated as metallic tin and/or antimony) of at least one of the metals tin and antimony, or at least one compound of at least one of the metals tin and antimony, and (3) from about 0.05 to 2% by weight, (calculated as alkali metal) of at least one of the alkali metals lithium, sodium, potassium and rubidium, or compound thereof, the amounts of said components (2) and (3) being based upon the total weight of said solid contact mass.

28 Claims, No Drawings

DIRECT CATALYTIC SYNTHESIS OF DIMETHYLDICHLOROSILANE FROM METHYL CHLORIDE AND SILICON

BACKGROUND OF THE INVENTION

Cross-Reference To Related Application

Our copending application, Ser No. 655,715, filed Sept. 28, 1984 and assigned to the assignee hereof.

Field of the Invention

The present invention relates to a process and catalyst for the direct synthesis of dimethyldichlorosilane from methyl chloride and silicon.

Description of the Prior Art

The industrial process for the production of organochlorosilanes and in particular of dimethyldichlorosilane, hereinafter referred to as DMCS, is well known and is described in detail in U.S. Pat. No. 2,380,995, as well as in the Walter Noll text, *Chemistry and Technology of Silicones,* pp. 26–41, Academic Press, Inc. (1968).

According to this so-called "direct synthesis" or "Rochow synthesis" process, the organochlorosilanes and, in particular, DMCS are directly produced by reacting methyl chloride over solid silicon in the presence of copper as a catalyst, in accordance with the reaction scheme:

$$2HC_3Cl + Si \rightarrow (CH_3)_2Cl_2Si.$$

In reality, other compounds are formed during such direct synthesis, especially $CH_3Cl_3Si$, hereinafter referred to as MTCS, and $(CH_3)_3ClSi$, hereinafter referred to as TMCS.

Other byproducts are also formed, such as, for example, $MeHSiCl_2$ and $Me_2HSiCl$ (Me=methyl) and non-volatile materials which are polysilanes, especially disilanes.

Among all of the compounds produced by the aforesaid direct synthesis, DMCS is the most desired. From this compound it is possible to prepare, after hydrolysis and polymerization, oils and gums which are base materials used in the production of silicones. Thus, DMCS is used for the preparation of polyorganosiloxane resins, as described in U.S. Pat. Nos. 2,258,218 to 2,258,222, for the preparation of oils described in U.S. Pat. Nos. 2,469,888 and 2,469,830 and for the preparation of polyorganosiloxane elastomers, described in U.S. Pat. No. 2,448,756.

The copper or copper compounds employed as the catalyst in the aforesaid direct synthesis reaction may be in the form of an alloy or in mechanical admixture with silicon, optionally deposited upon an inorganic carrier material.

It has also been proposed to add various additives to the copper to improve the yield of DMCS. These additives can be zinc or a zinc halide (U.S. Pat. No. 2,464,033), aluminum (U.S. Pat. Nos. 2,403,370 and 2,427,605), tin, manganese, nickel and silver (British Patent Specification No. 1,207,466), cobalt (British Patent Specification No. 907,161) and potassium chloride (U.S.S.R. Pat. No. 307,650).

The immediately aforesaid processes which employ such additives undoubtedly make it possible to improve the direct synthesis process, but they nevertheless suffer from at least one of the following disadvantages:

(1) the selectivity with respect to DMCS, measured as the average weight ratio MTCS/DMCS, and/or in terms of the molar percentage of DMCS relative to the total amount of silanes obtained, remains inadequate;

(2) the starting time and starting temperature of the reaction are too high;

(3) the mean activity of the catalyst system, also referred to as the productivity, measured in weight of methylchlorosilanes (MCS) obtained per hour and per kg of silicon introduced, and the maximum degree of conversion of the silicon, remain inadequate;

(4) the catalyst system is too sensitive to impurities; and (5) the formation of byproducts and in particular of disilanes remains high.

SUMMARY OF THE INVENTION

Accordingly, a major object of the present invention is the provision of an improved process/catalyst for the direct synthesis of DMCS from methyl chloride and silicon, which improved process is conspicuously devoid of the above disadvantages and drawbacks to date characterizing the state of the art, or which at very least dramatically reduces the adverse effects thereof.

Indeed, by use of the improved process/catalyst according to this invention, there are attained:

(i) a high mean selectivity with respect to DMCS, while at the same time increasing productivity, namely, increasing the amount of MCS produced per unit time and per unit contact mass;

(ii) a high initial selectivity upon commencement of the reaction, which can be maintained up to the final deterioration of the catalyst system;

(iii) a high maximum degree of conversion of the silicon;

(iv) a low proportion by weight of "non-volatile" products relative to the MCS obtained;

(v) a lesser sensitivity of the catalyst system to impurities which are a catalyst poison (in particular, to lead);

(vi) a reaction temperature which is not too high.

Briefly, the present invention features an improved process for the direct synthesis of dimethyldichlorosilane by reacting methyl chloride with a solid contact mass of silicon and a catalyst comprising (1) copper or a copper compound, (2) from about 30 to 1,000 ppm (calculated as tin and/or antimony metal) of at least one of the metals tin and antimony, or of a compound of tin and/or antimony, and (3) from about 0.05 to 2% by weight, preferably from 0.1 to 1% by weight (calculated as alkali metal) of at least one of the alkali metals lithium, sodium, potassium and rubidium, or compound thereof, relative to total amount by weight of the solid contact mass comprising the silicon and catalyst.

DETAILED DESCRIPTION OF THE INVENTION

More particularly according to the present invention, the subject catalyst is advantageously used in an amount ranging from 1 to 30% by weight, preferably from 5 to 12% by weight, of the total weight of the contact mass, i.e., the mixture of silicon plus catalyst.

The catalyst can be incorporated into the silicon in the form of an alloy or in mechanical admixture therewith.

In addition to metallic copper, a copper compound may also be used, notably a copper halide or a copper oxide, for example, CuO and $Cu_2O$, as described in U.S. Pat. No. 2,464,033.

Exemplary of the copper halides, cupric chloride or cuprous chloride are representative. It has in fact been shown according to the present invention, that best results, especially with respect to selectivity and degree of conversion of silicon, are obtained if the copper is introduced in the form of cuprous chloride or cupric chloride.

In a preferred embodiment of the invention, the catalyst further contains metallic zinc or a zinc compound, preferably zinc chloride or zinc oxide.

The zinc can be present in an amount by weight ranging from 0.1 to 3%, preferably from 0.2 to 1% (calculated as zinc metal) by weight, relative to the total weight of the solid contact mass. Up to 90%, preferably up to 50%, by weight of the zinc can be replaced by some other metal which catalyzes the chlorination of copper and/or which forms a eutectic, or a phase of low melting point, with the copper salts and/or the alkali metal salts.

As suitable such metals, representative are aluminum, cadmium, manganese, nickel and silver.

In addition to the pure alkali metals, Li, Na, K and Rb, whether used singly or in admixture thereof as the catalyst component (3), compounds of such alkali metals may also be used, notably the halides and preferably the chlorides. Rubidium, and to a lesser extent potassium, whether alone or in admixture, or in the form of compounds thereof, advantageously the chlorides, are the preferred catalyst components (3).

It is most preferred that the silicon be in particulate form, with the particle sizes thereof being such that the diameter of at least 50% by weight of the particles ranges from 10 to 500 microns.

Likewise, the catalyst is also preferably in the form of particles whose mean diameter advantageously ranges from 1 to 100 microns. Under these conditions of particle size of the contact mass, the direct synthesis reaction can be carried out using a contact mass in the form of a fluidized bed.

The direct synthesis according to the invention can typically be carried out in one of the following three types of apparatus: a reactor of the stirred bed type, such as that described in U.S. Pat. No. 2,449,821, a reactor of the fluidized bed type, as described in U.S. Pat. No. 2,389,931, or a rotary furnace.

The catalyst can also be used when deposited onto a particulate inorganic carrier material, such as sand, ground silica, silica gel, alumina, ground refractory brick, petroleum cracking catalysts, zeolites and calcined clays, as described in French Pat. No. 1,545,407.

The reaction advantageously takes place at a temperature ranging from 280° to 450° C., preferably from 290° to 370° C.

The reaction can be directly carried out at the temperature selected without commencing the reaction at a higher temperature, especially if the reaction temperature selected is on the order of 330° C. or more and the reaction is carried out in a fluidized bed.

The amount by weight of the alkali metal or alkali metal compound, calculated as the alkali metal, advantageously ranges from about 0.05 to 2% by weight relative to the weight of the total amount of contact mass, preferably from 0.1 to 1% by weight. Below 0.05%, the influence of the alkali metal is not genuinely detectable and above 2% by weight the alkali metal tends to poison the catalyst which significantly lowers the selectivity.

The amount by weight of tin and/or antimony, or tin compound and/or antimony compound (calculated as tin and/or antimony metal), advantageously ranges from about 30 to 1,000 ppm, preferably from 80 to 250 ppm, relative to the total amount by weight of contact mass.

It is necessary to use at least about 30 ppm of tin and/or antimony. It has in fact been shown according to the invention that the beneficial effects of the alkali metal or alkali metal compound are only obtained in the presence of tin and/or of antimony. Moreover, an amount by weight greater than 1,000 ppm would adversely affect the reaction and especially the selectivity thereof. Tin, which is the preferred metal, can be added in the form of bronze or as a tin compound, for example, tin chloride.

It too has been shown that if it is desired to carry out the reaction at a temperature below 350°–360° C., while retaining substantially the same advantages, zinc or a zinc compound, preferably zinc chloride, can be added in an amount by weight ranging from 0.1 to 3%, preferably from 0.2 to 1%, relative to the total amount of contact mass.

By using a catalyst according to the invention, very high selectivities can be achieved if the reaction is carried out in a stirred bed at a temperature of 330° to 350° C.

Thus, it is possible to obtain a mean ratio by weight of MTCS/DMCS typically ranging from 0.05 to 0.15, most commonly ranging from 0.07 to 1.2, and a mean molar % of DMCS, relative to the total silanes obtained, on the order of or greater than 80% and even as high as 90% or more, a maximum degree of conversion of silicon on the order of or greater than 55% and even as high as about 70% and a mean activity on the order of or greater than 125 g of MCS/h/kg of Si and even as high as 180 g of MCS/h/kg of Si, or more.

A selectivity on the order of or greater than 80% is strikingly unexpected and surprising in comparison with the selectivities which are obtained using catalyst masses of the same type, but not containing the alkali metal, as will be seen from the examples of French Pat. No. 1,545,407.

Moreover, if a contact mass according to the invention, but not containing tin and/or antimony is used, a contact mass which has very low activity and thus cannot be used industrially is obtained.

The percentage of non-volatiles obtained relative to the MCS obtained, can be on the order of 2% and is typically less than about 4%.

These results can be further improved if the reaction temperature is increased. Similar results are obtained if the reaction is carried out in a fluidized bed.

If the reaction is carried out at a temperature below 340° C. in a stirred bed, it is desirable to begin the reaction for about 20 to 30 minutes or so at a temperature above 340° C. This starting procedure is unnecessary if the reaction is carried out at a temperature above 340° C. in a stirred bed.

In order to further illustrate the present invention and the advantages thereof, the following specific examples are given, it being understood that same are intended only as illustrative and in nowise limitative.

In said examples which follow, unless otherwise indicated, a cylindrical pilot reactor having an internal diameter of 60 mm and a height of 250 mm height was used, equipped at its base with a sintered glass gas distributor. The silicon and the catalyst were introduced therein in the form of a powder of a mean size such that at least 50% of the particles ranged in size from 60 to 200 μm.

The reaction was carried out in a stirred bed and the reactor was equipped with an external heating element.

EXAMPLE 1

Catalyst system: CuCl/ZnCl$_2$/Sn/KCl

A powder consisting of 210 g of silicon, 16.37 g of cuprous chloride, 0.835 g of potassium chloride, 1.53 g of ZnCl$_2$ and 1.99 g of bronze containing 1.9% of tin, the percentage by weight of KCl relative to the total weight of the contact mass being 0.36, was introduced into a vertical cylindrical reactor made of glass and equipped with a metal stirrer and a sintered glass gas distributor.

The reactor was gradually heated to 200° C. under a stream of nitrogen. Thereafter, while continuing to raise the temperature of the reactor, the nitrogen valve was closed and the introduction of methyl chloride was commenced at a flow rate of 16 liters/hour, measured at 20° C.

After 1 hour of heating, regulated to 345° C., the flow rate of methyl chloride was increased to 26 liters/hour and maintained at this value until the reaction spontaneously completely stopped. The reaction temperature was 330° C.

This experiment produced chlorosilanes for 21 hours at a mean productivity or mean activity of 184 g of MCS per hour and per kg of Si introduced into the reactor. The mixture produced was characterized by a mean weight ratio MTCS/DMCS of 0.126 and a mean molar % of DMCS of 82.23.

The proportion of non-volatiles (polysilanes) obtained was 3.62% by weight.

Vapor phase chromatography evidenced the following mean molar selectivities:
Me$_3$SiCl: 5.58%
MeSiCl$_3$: 8.97%.

The maximum degree of conversion of the silicon was 84.3%.

EXAMPLE 2

Catalyst system: CuCl$_2$/ZnCl$_2$/Sn/RbCl

A powder consisting of 210 g of silicon, 1.53 g of ZnCl$_2$, 16.37 g of cuprous chloride, 1.355 g of potassium chloride and 1.99 g of bronze containing 1.9% of tin was introduced into a vertical cylindrical reactor made of glass and equipped with a metal stirrer and a sintered glass gas distributor.

The percentage by weight of RbCl relative to the total weight of the contact mass was 0.58.

The reactor was gradually heated to 200° C. under a stream of nitrogen. Thereafter, while continuing to raise the temperature of the reactor, the nitrogen valve was closed and the introduction of methyl chloride was commenced at a flow rate of 16 liters/hour, measured at 20° C.

After 1 hour of heating, regulated to 345° C., the flow rate of methyl chloride was increased to 26 liters/hour and maintained at this value until the reaction spontaneously stopped completely. The reaction temperature was 330° C.

This experiment produced chlorosilanes for 20 hours at a mean productivity or mean activity of 178 g of MCS per hour and per kg of silicon introduced into the reactor. The mixture produced was characterized by a mean weight ratio of methyltrichlorosilane to dimethyldichlorosilane, MTCS/DMCS, of 0.113 and a mean molar % of DMCS of 84.44%.

The proportion of non-volatiles (polysilanes) obtained was 3.16% (by weight).

Vapor phase chromatography evidenced the following mean molar selectivities:
Me$_3$SiCl: 4.32%
MeSiCl$_3$: 8.26%.

The maximum degree of conversion of the silicon was 77.5%.

EXAMPLES 3 and 4

The reaction was carried out in the same manner as in Example 1, using 210 g of silicon, except that the composition of the catalyst was altered.

The results obtained are reported in Table I below:

TABLE I

| EXAMPLE | 3 | 4 |
| --- | --- | --- |
| Catalyst (in g) | | |
| bronze (containing 1.9% of Sn) | 1.99 | 1.99 |
| CuCl | 16.37 | 16.37 |
| ZnCl$_2$ | 1.53 | 1.53 |
| KCl | 0.15 | 0.278 |
| T° C. | | |
| Start | 345 | 345 |
| Reaction | 330 | 330 |
| Productivity (g of MCS/h/kg of Si) | 162 | 165 |
| $\frac{MTCS}{DMCS}$, mean % by weight | 0.081 | 0.097 |
| Maximum degree of conversion of Si (%) | 72.4 | 62.7 |
| Mean selectivity, in molar %, of DMCS relative to the silanes obtained | 86.49 | 83.51 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the direct preparation of dimethyldichlorosilane from methyl chloride and silicon, comprising reacting methyl chloride with a solid contact mass comprising silicon and a catalytically effective amount of a catalyst which includes (1) elemental copper or a copper compound, (2) from about 30 to 1,000 ppm (calculated as metallic tin and/or antimony) of at least one of the metals tin and antimony, or at least one compound of at least one of the metals tin and antimony, and (3) from about 0.05 to 4% by weight (calculated as cesium metal) of cesium or a cesium compound, or admixture of cesium with up to 90% by weight of the admixture of one of the alkali metals lithium, sodium, potassium, rubidium or a compound of said alkali metals, the amounts of said components (2) and (3) being based upon the total weight of said solid contact mass.

2. The process as defined by claim 1, wherein said amount of tin and/or antimony ranges from 80 to 250 ppm.

3. The process as defined by claim 1, wherein said amount of alkali metal ranges from 0.1 to 1% by weight.

4. The process as defined by claim 1, said alkali metal comprising rubidium or potassium.

5. The process as defined by claim 1, said catalyst further comprising from 0.1 to 3% by weight (calculated as zinc metal) of zinc or a zinc compound, based on the total weight of said solid contact mass.

6. The process as defined by claim 5, wherein up to 90% by weight of the zinc is replaced by a metal which catalyzes the chlorination of the copper and/or which forms a eutectic or a phase of low melting point with copper salts and/or the alkali metal salts.

7. The process as defined by claim 6, wherein said replacement metal comprises aluminum, cadmium, manganese, nickel or silver.

8. The process as defined by claim 5, wherein said amount of zinc ranges from 0.2 to 1% by weight.

9. The process as defined by claim 1, said catalyst component (1) comprising metallic copper, cuprous chloride or cupric chloride.

10. The process as defined by claim 1, said catalyst comprising from 1 to 30% by weight of the total amount by weight of said solid contact mass.

11. The process as defined by claim 10, said catalyst comprising from 5 to 12% by weight of the total amount by weight of said solid contact mass.

12. The process as defined by claim 1, said solid contact mass comprising a plurality of particulates.

13. The process as defined by claim 12, said solid contact mass comprising intimate admixture of silicon particulates and catalyst particulates.

14. The process as defined by claim 13, at least 50 percent of said silicon particulates having particle sizes ranging from 10 to 500 microns and said catalyst particulates having particle sizes ranging from 1 to 100 microns.

15. The process as defined by claim 12, said particulates comprising an alloy of silicon and said catalyst.

16. The process as defined by claim 1, said catalyst being deposited upon particulate, inorganic carrier material.

17. The process as defined by claim 1, the temperature of reaction ranging from about 280° to 450° C.

18. The process as defined by claim 17, the temperature of reaction ranging from about 290° to 370° C.

19. The process as defined by claim 1, carried out in fluidized bed.

20. The process as defined by claim 1, carried out in stirred bed.

21. A catalyst composition comprising catalytically effective amounts of (1) elemental copper or a copper compound, (2) at least one of the metals tin and antimony, or at least one compound of at least one of the metals tin and antimony, and (3) at least one of the alkali metals lithium, sodium, potassium and rubidium, or compound thereof.

22. The catalyst composition as defined by claim 21, further comprising (4) zinc metal or a zinc compound.

23. The catalyst composition as defined by claim 22, up to 90% by weight of the zinc being replaced by a metal which catalyzes the chlorination of copper and/or which forms a eutectic or a phase of low melting point with copper salts and/or the alkali metal salts.

24. The catalyst composition as defined by claim 21, comprising a plurality of solid particulates.

25. The catalyst composition as defined by claim 21, alloyed with silicon.

26. A composition of matter comprising intimate admixture of silicon and the catalyst composition as defined by claim 21.

27. The composition of matter as defined by claim 26, comprising intimate admixture of a plurality of solid silicon particulates and a plurality of solid catalyst particulates.

28. A process for the direct preparation of dimethyldichlorosilane from methyl chloride and silicon, comprising reacting methyl chloride with a solid contact mass comprising silicon and a catalytically effective amount of a catalyst which includes (1) elemental copper or a copper compound, (2) from about 30 to 1,000 ppm (calculated as metallic tin and/or antimony) of at least one of the metals tin and antimony or at least one compound of at least one of the metals tin and antimony, (3) from about 0.05 to 4% by weight (calculated as cesium metal) of cesium or a cesium compound, or admixture of cesium with up to 90% by weight of the admixture of one of the alkali metals lithium, sodium, potassium, rubidium or a compound of said alkali metals, and (4) from 0.1 to 3% by weight (calculated as zinc metal) of zinc or a zinc compound, the amounts of said components (2), (3) and (4) being based upon the total weight of said solid contact mass.

* * * * *

UNITED STATES PATENT AND TRADEMARK OFFICE
CERTIFICATE OF CORRECTION

PATENT NO. : 4,656,301
DATED : April 7, 1987
INVENTOR(S) : Christian Prud'Homme et al.

It is certified that error appears in the above-identified patent and that said Letters Patent is hereby corrected as shown below:

Title page,
Item [30], Foreign Application Priority Data, please delete "83 15401" and insert therefore -- 83 15400 --.

Please delete the ABSTRACT in its entirety, and insert therefore

--

[57] ABSTRACT

Dimethyldichlorosilane is directly prepared from methyl chloride and silicon, in high productivity, selectivity and degree of silicon conversion, by reacting methyl chloride with a solid contact mass comprising silicon and a catalytically effective amount of a catalyst which includes (1) elemental copper or a copper compound, (2) from about 30 to 1,000 ppm (calculated as metallic tin and/or antimony) of at least one of the metals tin and antimony, or at least one compound of at least one of the metals tin and antimony, and (3) from about 0.05 to 4% by weight, (calculated as cesium metal) of cesium or a cesium compound, or admixture of cesium with up to 90% by weight of the admixture of lithium, sodium, potassium or rubidium, the amounts of said components (2) and (3) being based upon the total weight of said solid contact mass.

--

UNITED STATES PATENT AND TRADEMARK OFFICE
CERTIFICATE OF CORRECTION

PATENT NO. : 4,656,301
DATED : April 7, 1987
INVENTOR(S) : Christian Prud'Homme et al.

It is certified that error appears in the above-identified patent and that said Letters Patent is hereby corrected as shown below:

Column 1, line 11 through Column 6, line 34, please delete in its entirety, and insert therefore

--

Field of the Invention

The present invention relates to a process and catalyst for the direct synthesis of dimethyldichlorosilane from methyl chloride and silicon.

Description of the Prior Art

The industrial process for the production of organochlorosilanes and in particular of dimethyldichlorosilane, hereinafter referred to as DMCS, is well known and is described in detail in U.S. Pat. No. 2,380,995, as well as in the Walter Noll text, *Chemistry and Technology of Silicones*, pp. 26-41, Academic Press, Inc. (1968).

According to this so-called "direct synthesis" or "Rochow synthesis" process, the organochlorosilanes and, in particular, DMCS are directly produced by reacting methyl chloride over solid silicon in the presence of copper as a catalyst, in accordance with the reaction scheme:

In reality, other compounds are formed during such direct synthesis, especially $CH_3Cl_3Si$, hereinafter referred to as MTCS, and $(CH_3)_3ClSi$, hereinafter referred to as TMCS.

Other byproducts are also formed, such as, for example, $MeHSiCl_2$ and $Me_2HSiCl$ (Me=methyl) and nonvolatile materials which are polysilanes, especially disilanes.

UNITED STATES PATENT AND TRADEMARK OFFICE
CERTIFICATE OF CORRECTION

PATENT NO. : 4,656,301
DATED : April 7, 1987
INVENTOR(S) : Christian Prud'Homme et al.

It is certified that error appears in the above-identified patent and that said Letters Patent is hereby corrected as shown below:

A selectivity on the order of or greater than 90% is strikingly unexpected and surprising in comparison with the selectivities which are obtained using catalyst masses of the same type, but not containing cesium chloride, as will be seen from the examples of French Pat. No. 1,545,407.

Moreover, if a contact mass according to the invention, but not containing tin and/or antimony is used, a contact mass which has very low activity and thus cannot be used industrially is obtained, as shown by the comparative example which follows.

The percentage of non-volatiles obtained relative to the MCS obtained, can be on the order of 1% and is typically less than about 3%.

These results can be further improved if the reaction temperature is increased. Similar results are obtained if the reaction is carried out in a fluidized bed.

If the reaction is carried out at a temperature below 340° C. in a stirred bed, it is desirable to begin the reaction for about 20 to 30 minutes or so at a temperature above 340° C. This starting procedure is unnecessary if the reaction is carried out at a temperature above 340° C. in a stirred bed.

In order to further illustrate the present invention and the advantages thereof, the following specific examples are given, it being understood that same are intended only as illustrative and in nowise limitative.

In said examples which follow, unless otherwise indicated, a cylindrical pilot reactor having an internal diameter of 60 mm and a height of 250 mm height was used, equipped at its base with a sintered glass gas distributor. The silicon and the catalyst were introduced therein in the form of a powder of a mean size such that at least 50% of the particles ranged in size from 60 to 200 $\mu$m.

The reaction was carried out in a stirred bed and the reactor was equipped with an external heating element.

UNITED STATES PATENT AND TRADEMARK OFFICE
CERTIFICATE OF CORRECTION

PATENT NO.   : 4,656,301
DATED        : April 7, 1987
INVENTOR(S)  : Christian Prud'Homme et al.

It is certified that error appears in the above-identified patent and that said Letters Patent is hereby corrected as shown below:

EXAMPLE 1

Catalyst system: $CuCl_2/CsCl/Sn$ (at 360° C.)

A powder composed of 210 g of silicon, 22.23 g of cupric chloride, 1.902 g of cesium chloride and 1.984 g of bronze containing 1.9% of tin was introduced into a vertical cylindrical reactor (diameter = 60 mm) made of glass and equipped with a metal stirrer and a sintered glass gas distributor.

The reactor was gradually heated to 200° C. under a stream of nitrogen. Thereafter, while continuing to raise the temperature of the reactor, the nitrogen valve was closed and the introduction of methyl chloride was commenced, at a rate (measured at 20° C.) of 16 liters/hour.

After two hours of controlled heating at 360° C., the methyl chloride flow rate was increased to 39 liters/hour and maintained at this value until the reaction spontaneously completely stopped.

This experiment produced chlorosilanes for 13 hours at a mean productivity of 291 g per hour and per kg of silicon introduced into the reactor.

The mixture produced was characterized by a mean weight ratio of methyltrichlorosilane to dimethyldichlorosilane, MTCS/DMCS, of 0.039 and a mean molar % of DMCS of 92.7%.

The proportion of non-volatiles was 1.1% (by weight).

Vapor phase chromatography evidenced the following mean molar selectivities:
$Me_3SiCl$: 1.58%
$MeSiCl_3$: 3.15%

The maximum degree of conversion of the silicon was 83%.

UNITED STATES PATENT AND TRADEMARK OFFICE
CERTIFICATE OF CORRECTION

PATENT NO.    : 4,656,301
DATED         : April 7, 1987
INVENTOR(S)   : Christian Prud'Homme et al.

It is certified that error appears in the above-identified patent and that said Letters Patent is hereby corrected as shown below:

EXAMPLE 2

Catalyst system: CuCl/CsCl/Sn (at 360° C.)

A powder composed of 210 g of silicon, 16.37 g of cuprous chloride, 1.89 g of cesium chloride and 2.23 g of bronze containing 1.9% of tin was introduced into a vertical cylindrical reactor (diameter=60 mm) made of glass and equipped with a metal stirrer and a sintered glass gas distributor.

The reactor was gradually heated to 200° C. under a stream of nitrogen. Thereafter, while continuing to heat, the nitrogen flow was terminated and the introduction of methyl chloride was commenced at a flow rate (at 20° C.) of 16 liters/hour. Two hours after the temperature had become stabilized at 360° C., the methyl chloride flow rate was increased to 39 liters/hour and maintained at this value until the reaction spontaneously was terminated.

This experiment produced chlorosilanes for 14 hours at a mean productivity of 269 g per hour and per kg of silicon introduced into the reactor.

The mixture produced was characterized by a mean weight ratio of methyltrichlorosilane to dimethyldichlorosilane, MTCS/DMCS, of 0.036 and a mean molar % of DMCS of 93.2.

The proportion of non-volatiles was 1.3% (by weight).

Vapor phase chromatography evidenced the following mean molar selectivities:

$Me_3SiCl$: 1.77%

$MeSiCl_3$: 2.91%

The maximum degree of conversion of the silicon was 82%.

UNITED STATES PATENT AND TRADEMARK OFFICE
CERTIFICATE OF CORRECTION

PATENT NO.    : 4,656,301
DATED         : April 7, 1987
INVENTOR(S)   : Christian Prud'Homme et al.

It is certified that error appears in the above-identified patent and that said Letters Patent is hereby corrected as shown below:

The temperature of the reactor was then regulated to 345° C. and maintained at this value for about 1 hour before it was lowered to 330° C.

The methyl chloride flow rate was then raised to 26 liters/hour.

Heating at 330° C., and stirring, were continued until the reaction stopped completely and spontaneously.

This experiment produced chlorosilanes for 20 hours at a mean productivity of 175 g per hour and per kg of silicon introduced into the reactor.

The mixture produced was characterized by a mean weight ratio of MTCS/DMCS of 0.042 and a mean molar % of DMCS of 91.78.

The proportion of non-volatiles was 2.3% (by weight).

Vapor phase chromatography evidenced the following mean molar selectivities:
$Me_3SiCl$: 2.5%
$MeSiCl_3$: 3.36%
$Me_2SiCl_2$: 91.78%

The maximum degree of conversion of the silicon was 77%.

EXAMPLES 6 to 9

The reaction was carried out in the same manner as in Example 1, with 210 g of silicon, except that the reaction temperature and the composition of the catalyst were changed.

UNITED STATES PATENT AND TRADEMARK OFFICE
CERTIFICATE OF CORRECTION

PATENT NO.    : 4,656,301
DATED         : April 7, 1987
INVENTOR(S)   : Christian Prud'Homme et al.

It is certified that error appears in the above-identified patent and that said Letters Patent is hereby corrected as shown below:

The results obtained are reported in Table I below:

TABLE I

| EXAMPLE | 6 | 7 | 8 | 9 |
|---|---|---|---|---|
| Catalyst (in g) | | | | |
| Cu: | 0 | 0 | 23 | 23 |
| CuCl: | 16.37 | 16.4 | 0 | 0 |
| Sn*: | 2.23 | 2 | 2 | 2 |
| ZnCl$_2$: | 0 | 1.5 | 1.5 | 3 |
| CsCl: | 1.89 | 1.9 | 1.9 | 1.9 |
| T °C | | | | |
| Start | none | 345 | 345 | 345 |
| Reaction | 360 | 330 | 330 | 330 |
| Productivity (g of MCS/h/kg of Si) | 234 | 175 | 114 | 127 |
| MTCS/DMCS, mean % by weight | 0.042 | 0.042 | 0.083 | 0.068 |
| Mean selectivity (mole %) relative to the silanes obtained | 92.3 | 91.8 | 89 | 90.2 |
| % by weight of non-volatiles relative to the MCS formed | 1.3 | 2.3 | 3.1 | |
| Maximum degree of conversion of Si (in %) | 74 | 78 | 85 | 88 |

*The figures shown are the amount by weight of bronze (containing 1.9% of Sn) used.

--

Column 8,
Line 5 through line 7, please delete "at least one of the alkali metals lithium, sodium, potasium and rubidium, or compound thereof", and insert therefore -- cesium metal or cesium compound --;
Line 14, please delete "alkali metal salts", and insert therefore -- cesium compound --;
Line 15, before "The", please insert -- The catalyst composition as defined by Claim 21, up to 90% by weight (calculated as cesium metal) of the cesium compound being replaced by at least one of the alkali metals lithium, sodium, potassium and rubidium, or by a compound of such alkali metals.

25. --

UNITED STATES PATENT AND TRADEMARK OFFICE
CERTIFICATE OF CORRECTION

PATENT NO.    : 4,656,301
DATED         : April 7, 1987
INVENTOR(S)   : Christian Prud ' Homme et al.

It is certified that error appears in the above-identified patent and that said Letters Patent is hereby corrected as shown below:

Line 17, please delete "25", and insert therefore -- 26 --;
Line 19, delete "26", and insert therefore -- 27 --;
Line 22, please delete "27", and insert therefore -- 28 --; delete "26" and insert therefore -- 27 --;
Line 26, please delete "28", and insert therefore -- 29 --.

Signed and Sealed this

Twelfth Day of November, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 4,656,301  
DATED : April 7, 1987  
INVENTOR(S) : Christian Prud ' Homme et al.

It is certified that error appears in the above-identified patent and that said Letters Patent is hereby corrected as shown below:

<u>Title page,</u>  
Item [30], Foreign Application Priority Data, please delete "83 15401" and insert therefore -- 83 15400 --.

Please delete the ABSTRACT in its entirety, and insert therefore

--

[57] ABSTRACT

Dimethyldichlorosilane is directly prepared from methyl chloride and silicon, in high productivity, selectivity and degree of silicon conversion, by reacting methyl chloride with a solid contact mass comprising silicon and a catalytically effective amount of a catalyst which includes (1) elemental copper or a copper compound, (2) from about 30 to 1,000 ppm (calculated as metallic tin and/or antimony) of at least one of the metals tin and antimony, or at least one compound of at least one of the metals tin and antimony, and (3) from about 0.05 to 4% by weight, (calculated as cesium metal) of cesium or a cesium compound, or admixture of cesium with up to 90% by weight of the admixture of lithium, sodium, potassium or rubidium, the amounts of said components (2) and (3) being based upon the total weight of said solid contact mass.

--

UNITED STATES PATENT AND TRADEMARK OFFICE
CERTIFICATE OF CORRECTION

PATENT NO. : 4,656,301
DATED : April 7, 1987
INVENTOR(S) : Christian Prud ' Homme et al.

Page 2 of 17

It is certified that error appears in the above-identified patent and that said Letters Patent is hereby corrected as shown below:

Column 1, line 11, through Column 6, line 34,
Please delete in its entirety, and insert therefore

Field of the Invention

The present invention relates to a process and catalyst for the direct synthesis of dimethyldichlorosilane from methyl chloride and silicon.

Description of the Prior Art

The industrial process for the production of organochlorosilanes and in particular of dimethyldichlorosilane, hereinafter referred to as DMCS, is well known and is described in detail in U.S. Pat. No. 2,380,995, as well as in the Walter Noll text, *Chemistry and Technology of Silicones*, pp. 26–41, Academic Press, Inc. (1968).

According to this so-called "direct synthesis" or "Rochow synthesis" process, the organochlorosilanes and, in particular, DMCS are directly produced by reacting methyl chloride over solid silicon in the presence of copper as a catalyst, in accordance with the reaction scheme:

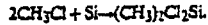
$2CH_3Cl + Si \rightarrow (CH_3)_2Cl_2Si.$

In reality, other compounds are formed during such direct synthesis, especially $CH_3Cl_3Si$, hereinafter referred to as MTCS, and $(CH_3)_3ClSi$, hereinafter referred to as TMCS.

Other byproducts are also formed, such as, for example, $MeHSiCl_2$ and $Me_2HSiCl$ (Me = methyl) and nonvolatile materials which are polysilanes, especially disilanes.

UNITED STATES PATENT AND TRADEMARK OFFICE
CERTIFICATE OF CORRECTION

PATENT NO. : 4,656,301
DATED : April 7, 1987
INVENTOR(S) : Christian Prud ' Homme et al.

It is certified that error appears in the above-identified patent and that said Letters Patent is hereby corrected as shown below:

Among all of the compounds produced by the aforesaid direct synthesis, DMCS is the most desired. From this compound it is possible to prepare, after hydrolysis and polymerization, oils and gums which are base materials used in the production of silicones. Thus, DMCS is used for the preparation of polyorganosiloxane resins, as described in U.S. Pat. Nos. 2,258,218 to 2,258,222, for the preparation of oils described in U.S. Pat. Nos. 2,469,888 and 2,469,830 and for the preparation of polyorganosiloxane elastomers, described in U.S. Pat. No. 2,448,756.

The copper or copper compounds employed as the catalyst in the aforesaid direct synthesis reaction may be in the form of an alloy or in mechanical admixture with silicon, optionally deposited upon an inorganic carrier material.

It has also been proposed to add various additives to the copper to improve the yield of DMCS. These additives can be zinc or a zinc halide (U.S. Pat. No. 2,464,033), aluminum (U.S. Pat. Nos. 2,403,370 and 2,427,605), tin, manganese, nickel and silver (British Patent Specification No. 1,207,466), cobalt (British Patent Specification No. 907,161) and potassium chloride (U.S.S.R. Pat. No. 307,650).

The immediately aforesaid processes which employ such additives undoubtedly make it possible to improve the direct synthesis process, but they nevertheless suffer from at least one of the following disadvantages:

(1) the selectivity with respect to DMCS, measured as the average weight ratio MTCS/DMCS, and/or in terms of the molar percentage of DMCS relative to the total amount of silanes obtained, remains inadequate;

(2) the starting time and starting temperature of the reaction are too high;

(3) the mean activity of the catalyst system, also referred to as the productivity, measured in weight of methylchlorosilanes (MCS) obtained per hour and per kg of silicon introduced, and the maximum degree of conversion of the silicon, remain inadequate;

UNITED STATES PATENT AND TRADEMARK OFFICE
CERTIFICATE OF CORRECTION

PATENT NO. : 4,656,301
DATED : April 7, 1987
INVENTOR(S) : Christian Prud ' Homme et al.

It is certified that error appears in the above-identified patent and that said Letters Patent is hereby corrected as shown below:

(4) the catalyst system is too sensitive to impurities; and (5) the formation of byproducts and in particular of disilanes remains high.

SUMMARY OF THE INVENTION

Accordingly, a major object of the present invention is the provision of an improved process/catalyst for the direct synthesis of DMCS from methyl chloride and silicon, which improved process is conspicuously devoid of the above disadvantages and drawbacks to date characterizing the state of the art, or which at very least dramatically reduces the adverse effects thereof.

Indeed, by use of the improved process/catalyst according to this invention, there are attained:

(i) a high mean selectivity with respect to DMCS, while at the same time increasing productivity, namely, increasing the amount of MCS produced per unit time and per unit contact mass;

(ii) a high initial selectivity upon commencement of the reaction, which can be maintained up to the final deterioration of the catalyst system;

(iii) a high maximum degree of conversion of the silicon;

(iv) a low proportion by weight of "non-volatile" products relative to the MCS obtained;

(v) a lesser sensitivity of the catalyst system to impurities which are a catalyst poison (in particular, to lead);

(vi) a reaction temperature which is not too high.

Briefly, the present invention features an improved process for the direct synthesis of dimethyldichlorosilane by reacting methyl chloride with a solid contact mass of silicon and a catalyst comprising (1) copper or a copper compound, (2) from about 30 to 1,000 ppm (calculated as tin and/or antimony metal) of at least one of the metals tin and antimony, or of a compound of tin and/or antimony, and (3) from about 0.05 to 4% by weight, preferably from 0.1 to 1.5% by weight (calculated as cesium metal) of cesium or of a cesium com-

UNITED STATES PATENT AND TRADEMARK OFFICE
CERTIFICATE OF CORRECTION

PATENT NO. : 4,656,301
DATED : April 7, 1987
INVENTOR(S) : Christian Prud ' Homme et al.

It is certified that error appears in the above-identified patent and that said Letters Patent is hereby corrected as shown below:

pound, or admixture of cesium with up to 90% by weight of the admixture of lithium, sodium, potassium or rubidium, relative to total amount by weight of the solid contact mass comprising the silicon and catalyst.

DETAILED DESCRIPTION OF THE INVENTION

More particularly according to the present invention, the subject catalyst is advantageously used in an amount ranging from 1 to 30% by weight, preferably from 5 to 12% by weight, of the total weight of the contact mass, i.e., the mixture of silicon plus catalyst.

The catalyst can be incorporated into the silicon in the form of an alloy or in mechanical admixture therewith.

In addition to metallic copper, a copper compound may also be used, notably a copper halide or a copper oxide, for example, $CuO$ and $Cu_2O$, as described in U.S. Pat. No. 2,464,033.

Exemplary of the copper halides, cupric chloride or cuprous chloride are representative. It has in fact been shown according to the present invention, that best results, especially with respect to selectivity and degree of conversion of silicon, are obtained if the copper is introduced in the form of cuprous chloride or cupric chloride.

In a preferred embodiment of the invention, the catalyst further contains metallic zinc or a zinc compound, preferably zinc chloride or zinc oxide.

The zinc can be present in an amount by weight ranging from 0.1 to 3%, preferably from 0.2 to 1% (calculated as zinc metal) by weight, relative to the total weight of the solid contact mass. Up to 90%, preferably up to 50%, by weight of the zinc can be replaced by some other metal which catalyzes the chlorination of copper and/or which forms a eutectic, or a phase of low melting point, with the copper salts and/or the cesium compound As suitable such metals, representative are aluminum, cadmium, manganese, nickel and silver.

UNITED STATES PATENT AND TRADEMARK OFFICE
CERTIFICATE OF CORRECTION

PATENT NO. : 4,656,301
DATED : April 7, 1987
INVENTOR(S) : Christian Prud' Homme et al.

It is certified that error appears in the above-identified patent and that said Letters Patent is hereby corrected as shown below:

In addition to pure cesium, the cesium compounds may be used, such as the halides thereof, and preferably cesium chloride.

It is most preferred that the silicon be in particulate form, with the particle sizes thereof being such that the diameter of at least 50% by weight of the particles ranges from 10 to 500 microns.

Likewise, the catalyst is also preferably in the form of particles whose mean diameter advantageously ranges from 1 to 100 microns. Under these conditions of particle size of the contact mass, the direct synthesis reaction can be carried out using a contact mass in the form of a fluidized bed.

The direct synthesis according to the invention can typically be carried out in one of the following three types of apparatus: a reactor of the stirred bed type, such as that described in U.S. Pat. No. 2,449,821, a reactor of the fluidized bed type, as described in U.S. Pat. No. 2,389,931, or a rotary furnace.

The catalyst can also be used when deposited onto a particulate inorganic carrier material, such as sand, ground silica, silica gel, alumina, ground refractory brick, petroleum cracking catalysts, zeolites and calcined clays, as described in French Pat. No. 1,545,407.

The reaction advantageously takes place at a temperature ranging from 280° to 450° C., preferably from 290° to 370° C.

The reaction can be directly carried out at the temperature selected without commencing the reaction at a higher temperature, especially if the reaction temperature selected is on the order of 330° C. or more and the reaction is carried out in a fluidized bed.

The amount by weight of the cesium or cesium compound, calculated as cesium metal, advantageously ranges from about 0.05 to 4% by weight relative to the weight of the total amount of contact mass, preferably from 0.1 to 1.5% by weight. Below 0.05%, the influence of the cesium is not genuinely detectable and above 4% by weight the cesium tends to poison the catalyst which significantly lowers the selectivity.

The amount by weight of tin and/or antimony, or tin compound and/or antimony compound (calculated as tin and/or antimony metal), advantageously ranges

UNITED STATES PATENT AND TRADEMARK OFFICE
CERTIFICATE OF CORRECTION

PATENT NO. : 4,656,301
DATED : April 7, 1987
INVENTOR(S) : Christian Prud' Homme et al.

It is certified that error appears in the above-identified patent and that said Letters Patent is hereby corrected as shown below:

from about 30 to 1,000 ppm, preferably from 80 to 250 ppm, relative to the total amount of contact mass.

It is necessary to use at least about 30 ppm of tin and/or antimony. It has in fact been shown according to the invention that the beneficial effects of the cesium or cesium compound are only obtained in the presence of tin and/or of antimony. Moreover, an amount by weight greater than 1,000 ppm would adversely affect the reaction and especially the selectivity thereof. Tin, which is the preferred metal, can be added in the form of bronze or as a tin compound, for example, tin chloride.

It too has been shown that if it is desired to carry out the reaction at a temperature below 350°-360° C., while retaining substantially the same advantages, zinc or a zinc compound, preferably zinc chloride, can be added in an amount by weight ranging from 0.1 to 3%, preferably from 0.2 to 1%, relative to the total amount of contact mass.

It has also been shown that up to 90% and preferably up to 50% by weight (calculated as cesium metal) of the cesium or cesium compound can be replaced by a different alkali metal selected from among lithium, sodium or potassium and rubidium, or by a compound, e.g., a salt, of such an alkali metal. Though generally lesser results are obtained than when using cesium or a cesium compound alone, the partial replacement of same by potassium or sodium makes it possible to significantly reduce the cost of the catalyst.

By using a catalyst according to the invention, very high selectivities can be achieved if the reaction is carried out in a stirred bed at a temperature of 330° to 350° C.

Thus, it is possible to obtain a mean ratio by weight of MTCS/DMCS on the order of, or less than, 0.05, and even as low as 0.03, and a mean molar % of DMCS, relative to the total silanes obtained, on the order of or greater than 90% and even as high as 96%, a maximum degree of conversion of silicon on the order of or greater than 70% and even as high as about 85% and a mean activity on the order of or greater than 125 g of MCS/h/kg of Si and even as high as 180 g of MCS/h/kg of Si, or more.

UNITED STATES PATENT AND TRADEMARK OFFICE
CERTIFICATE OF CORRECTION

PATENT NO.    : 4,656,301
DATED         : April 7, 1987
INVENTOR(S)   : Christian Prud ' Homme et al.

It is certified that error appears in the above-identified patent and that said Letters Patent is hereby corrected as shown below:

A selectivity on the order of or greater than 90% is strikingly unexpected and surprising in comparison with the selectivities which are obtained using catalyst masses of the same type, but not containing cesium chloride, as will be seen from the examples of French Pat. No. 1,545,407.

Moreover, if a contact mass according to the invention, but not containing tin and/or antimony is used, a contact mass which has very low activity and thus cannot be used industrially is obtained, as shown by the comparative example which follows.

The percentage of non-volatiles obtained relative to the MCS obtained, can be on the order of 1% and is typically less than about 3%.

These results can be further improved if the reaction temperature is increased. Similar results are obtained if the reaction is carried out in a fluidized bed.

If the reaction is carried out at a temperature below 340° C. in a stirred bed, it is desirable to begin the reaction for about 20 to 30 minutes or so at a temperature above 340° C. This starting procedure is unnecessary if the reaction is carried out at a temperature above 340° C. in a stirred bed.

In order to further illustrate the present invention and the advantages thereof, the following specific examples are given, it being understood that same are intended only as illustrative and in nowise limitative.

In said examples which follow, unless otherwise indicated, a cylindrical pilot reactor having an internal diameter of 60 mm and a height of 250 mm height was used, equipped at its base with a sintered glass gas distributor. The silicon and the catalyst were introduced therein in the form of a powder of a mean size such that at least 50% of the particles ranged in size from 60 to 200 μm.

The reaction was carried out in a stirred bed and the reactor was equipped with an external heating element.

UNITED STATES PATENT AND TRADEMARK OFFICE
CERTIFICATE OF CORRECTION

PATENT NO. : 4,656,301
DATED : April 7, 1987
INVENTOR(S) : Christian Prud'Homme et al.

It is certified that error appears in the above-identified patent and that said Letters Patent is hereby corrected as shown below:

EXAMPLE 1

Catalyst system: $CuCl_2/CsCl/Sn$ (at 360° C.)

A powder composed of 210 g of silicon, 22.23 g of cupric chloride, 1.902 g of cesium chloride and 1.984 g of bronze containing 1.9% of tin was introduced into a vertical cylindrical reactor (diameter = 60 mm) made of glass and equipped with a metal stirrer and a sintered glass gas distributor.

The reactor was gradually heated to 200° C. under a stream of nitrogen. Thereafter, while continuing to raise the temperature of the reactor, the nitrogen valve was closed and the introduction of methyl chloride was commenced, at a rate (measured at 20° C.) of 16 liters/hour.

After two hours of controlled heating at 360° C., the methyl chloride flow rate was increased to 39 liters/hour and maintained at this value until the reaction spontaneously completely stopped.

This experiment produced chlorosilanes for 13 hours at a mean productivity of 291 g per hour and per kg of silicon introduced into the reactor.

The mixture produced was characterized by a mean weight ratio of methyltrichlorosilane to dimethyldichlorosilane, MTCS/DMCS, of 0.039 and a mean molar % of DMCS of 92.7%.

The proportion of non-volatiles was 1.1% (by weight).

Vapor phase chromatography evidenced the following mean molar selectivities:
$Me_3SiCl$: 1.58%
$MeSiCl_3$: 3.15%

The maximum degree of conversion of the silicon was 83%.

UNITED STATES PATENT AND TRADEMARK OFFICE
CERTIFICATE OF CORRECTION

PATENT NO. : 4,656,301
DATED : April 7, 1987
INVENTOR(S) : Christian Prud ' Homme et al.

It is certified that error appears in the above-identified patent and that said Letters Patent is hereby corrected as shown below:

EXAMPLE 2

Catalyst system: CuCl/CsCl/Sn (at 360° C.)

A powder composed of 210 g of silicon, 16.37 g of cuprous chloride, 1.89 g of cesium chloride and 2.23 g of bronze containing 1.9% of tin was introduced into a vertical cylindrical reactor (diameter=60 mm) made of glass and equipped with a metal stirrer and a sintered glass gas distributor.

The reactor was gradually heated to 200° C. under a stream of nitrogen. Thereafter, while continuing to heat, the nitrogen flow was terminated and the introduction of methyl chloride was commenced at a flow rate (at 20° C.) of 16 liters/hour. Two hours after the temperature had become stabilized at 360° C., the methyl chloride flow rate was increased to 39 liters/hour and maintained at this value until the reaction spontaneously was terminated.

This experiment produced chlorosilanes for 14 hours at a mean productivity of 269 g per hour and per kg of silicon introduced into the reactor.

The mixture produced was characterized by a mean weight ratio of methyltrichlorosilane to dimethyldichlorosilane, MTCS/DMCS, of 0.036 and a mean molar % of DMCS of 93.2.

The proportion of non-volatiles was 1.3% (by weight).

Vapor phase chromatography evidenced the following mean molar selectivities:

$Me_3SiCl$: 1.77%
$MeSiCl_3$: 2.91%

The maximum degree of conversion of the silicon was 82%.

UNITED STATES PATENT AND TRADEMARK OFFICE
CERTIFICATE OF CORRECTION

PATENT NO. : 4,656,301
DATED : April 7, 1987
INVENTOR(S) : Christian Prud ' Homme et al.

It is certified that error appears in the above-identified patent and that said Letters Patent is hereby corrected as shown below:

EXAMPLE 3

Catalyst system: CuCl/CsCl/Sn (at 360° C.)

A powder composed of 210 g of silicon, 1.89 g of cesium chloride, 16.37 g of cuprous chloride and 2.23 g of bronze containing 1.9% of tin was introduced into a vertical cylindrical reactor (diameter=60 mm) made of glass and equipped with a metal stirrer and a sintered glass gas distributor.

The reactor was heated gradually to 200° C. under a stream of nitrogen. Thereafter, while continuing to increase the temperature of the reactor, the nitrogen valve was closed and the introduction of methyl chloride was commenced at a flow rate of 16 liters/hour (at about 20° C.). The temperature of the reactor was then regulated to 360° C. and maintained at this value until the reaction terminated completely.

This experiment produced chlorosilanes for 20 hours at a mean productivity of 167 g per hour and per kg of silicon introduced into the reactor.

The mixture produced was characterized by a mean weight ratio of MTCS/DMCS of 0.045 and a mean molar % of DMCS of 92.5.

The proportion of non-volatiles was 1% (by weight).

Vapor phase chromatography evidenced the following mean molar selectivities:

$Me_3SiCl$: 1.81%
$MeSiCl_3$: 3.63%

The maximum degree of conversion of the silicon was 74%.

EXAMPLE 4

Catalyst system: Cu/ZnCl$_2$/CsCl/Sn (at 345° C.)

A powder composed of 210 g of silicon, 3.14 g of zinc chloride, 22.9 g of copper metal powder, 1.89 g of cesium chloride and 1.99 g of bronze containing 1.9% of tin was introduced into a vertical cylindrical reactor (diameter=60 mm) made of glass and equipped with a metal stirrer and a sintered glass gas distributor.

UNITED STATES PATENT AND TRADEMARK OFFICE
CERTIFICATE OF CORRECTION

PATENT NO. : 4,656,301
DATED : April 7, 1987
INVENTOR(S) : Christian Prud ' Homme et al.

It is certified that error appears in the above-identified patent and that said Letters Patent is hereby corrected as shown below:

The reactor was gradually heated to 200° C. under a stream of nitrogen. Thereafter, while continuing the heating, the nitrogen flow was terminated and the methyl chloride was introduced at a flow rate of 16 liters/hour. The temperature of the reactor was then regulated to 345° C. About 4 hours after beginning the reaction, the methyl chloride flow rate was increased gradually to 39 liters/hour. These conditions were then maintained until the reaction stopped completely. This experiment produced chlorosilanes for 18 hours with a mean productivity of 215 g per hour and per kg of silicon introduced into the reactor.

The mixture produced was characterized by a mean weight ratio of MTCS/DMCS of 0.072 and a mean molar % of DMCS of 89.46.

The proportion of non-volatiles was 1.81% (by weight).

Vapor phase chromatography evidenced the following mean molar selectivities:

$Me_3SiCl$: 3.2%

$MeSiCl_3$: 5.62%

The maximum degree of conversion of the silicon was 85%.

EXAMPLE 5

Catalyst system: $CuCl/ZnCl_2/CsCl/Sn$ (at 330° C.)

A powder composed of 210 g of silicon, 16.4 g of cuprous chloride, 1.9 g of cesium chloride, 1.53 g of zinc chloride and 1.99 g of bronze containing 1.9% of tin was introduced into a vertical cylindrical reactor (diameter=60 mm) made of glass and equipped with a metal stirrer and a sintered glass gas distributor.

The reactor was gradually heated to 200° C. under a stream of nitrogen. Thereafter, while continuing the heating, the nitrogen flow was terminated and the introduction of methyl chloride was commenced at a flow rate of 16 liters/hour.

UNITED STATES PATENT AND TRADEMARK OFFICE
CERTIFICATE OF CORRECTION

PATENT NO.  : 4,656,301
DATED       : April 7, 1987
INVENTOR(S) : Christian Prud ' Homme et al.

It is certified that error appears in the above-identified patent and that said Letters Patent is hereby corrected as shown below:

The temperature of the reactor was then regulated to 345° C. and maintained at this value for about 1 hour before it was lowered to 330° C.

The methyl chloride flow rate was then raised to 26 liters/hour.

Heating at 330° C., and stirring, were continued until the reaction stopped completely and spontaneously.

This experiment produced chlorosilanes for 20 hours at a mean productivity of 175 g per hour and per kg of silicon introduced into the reactor.

The mixture produced was characterized by a mean weight ratio of MTCS/DMCS of 0.042 and a mean molar % of DMCS of 91.78.

The proportion of non-volatiles was 2.3% (by weight).

Vapor phase chromatography evidenced the following mean molar selectivities:

$Me_3SiCl$: 2.5%
$MeSiCl_3$: 3.36%
$Me_2SiCl_2$: 91.78%

The maximum degree of conversion of the silicon was 77%.

EXAMPLES 6 to 9

The reaction was carried out in the same manner as in Example 1, with 210 g of silicon, except that the reaction temperature and the composition of the catalyst were changed.

UNITED STATES PATENT AND TRADEMARK OFFICE
CERTIFICATE OF CORRECTION

PATENT NO. : 4,656,301
DATED : April 7, 1987
INVENTOR(S) : Christian Prud' Homme et al.

It is certified that error appears in the above-identified patent and that said Letters Patent is hereby corrected as shown below:

The results obtained are reported in Table I below:

TABLE I

| EXAMPLE | 6 | 7 | 8 | 9 |
|---|---|---|---|---|
| Catalyst (in g) | | | | |
| Cu | 0 | 0 | 23 | 23 |
| CuCl | 16.37 | 16.4 | 0 | 0 |
| Sn*: | 2.23 | 2 | 2 | 2 |
| ZnCl$_2$: | 0 | 1.5 | 1.5 | 3 |
| CsCl: | 1.89 | 1.9 | 1.9 | 1.9 |
| T °C | | | | |
| Start | none | 345 | 345 | 345 |
| Reaction | 360 | 330 | 330 | 330 |
| Productivity (g of MCS/h/kg of Si) | 234 | 175 | 114 | 127 |
| $\frac{MTCS}{DMCS}$, mean % by weight | 0.042 | 0.042 | 0.083 | 0.068 |
| Mean selectivity (mole %) relative to the silanes obtained | 92.3 | 91.8 | 89 | 90.2 |
| % by weight of non-volatiles relative to the MCS formed | 1.3 | 2.3 | 3.1 | |
| Maximum degree of conversion of Si (in %) | 74 | 78 | 85 | 88 |

*The figures shown are the amount by weight of bronze (containing 1.9% of Sn) used.

Page 14 of 17

UNITED STATES PATENT AND TRADEMARK OFFICE
CERTIFICATE OF CORRECTION

PATENT NO. : 4,656,301
DATED : April 7, 1987
INVENTOR(S) : Christian Prud'Homme et al.

It is certified that error appears in the above-identified patent and that said Letters Patent is hereby corrected as shown below:

COMPARATIVE EXAMPLE

The process was carried out in accordance with the method of Example 5, using 210 of silicon, except that the composition of the catalyst was altered. The results obtained are reported in Table II below:

TABLE II

| COMPARATIVE EXAMPLE | 1 |
|---|---|
| Catalyst (in g) | |
| Cu: | 0 |
| CuCl: | 16.37 |
| Bronze containing | |
| 1.9% of Sn: | 0 |
| $ZnCl_2$: | 1.53 |
| CsCl: | 1.92 |
| T °C. | |
| Start | 345 |
| Reaction | 330 |
| Productivity (g of MCS/h/kg of Si) | 25 |
| $\frac{MTCS}{DMCS}$, mean % by weight | 0.076 |
| Mean selectivity (mole %) relative to the silanes obtained | 77.6 |
| % by weight of non-volatiles relative to the MCS formed | 1.5 |
| Maximum degree of conversion of Si (in %) | 4 |

This comparative example evidences that in the presence of cesium, but in the absence of tin and/or antimony, a contact mass of very low activity was obtained.

UNITED STATES PATENT AND TRADEMARK OFFICE
CERTIFICATE OF CORRECTION

PATENT NO. : 4,656,301
DATED : April 7, 1987
INVENTOR(S) : Christian Prud ' Homme et al.

It is certified that error appears in the above-identified patent and that said Letters Patent is hereby corrected as shown below:

Column 6,
Line 63, through Column 7, line 12, please delete in its entirety, and insert therefore

--

3. The process as defined by claim 1, wherein said amount of cesium ranges from 0.1 to 1.5% by weight.

4. The process as defined by claim 1, said catalyst further comprising from 0.1 to 3% by weight (calculated as zinc metal) of zinc or a zinc compound, based on the total weight of said solid contact mass.

5. The process as defined by claim 4, wherein up to 90% by weight of the zinc is replaced by a metal which catalyzes the chlorination of the copper and/or which forms a eutectic or a phase of low melting point with copper salts and/or the cesium compound.

6. The process as defined by claim 5, wherein said replacement metal comprises aluminum, cadminm, manganese, nickel or silver.

7. The process as defined by claim 1, wherein said component (3) comprises admixture of cesium with up to 90% by weight of the admixture of lithium, sodium, potassium, rubidium, or compound thereof.

8. The process as defined by claim 4, wherein said amount of zinc ranges from 0.2 to 1% by weight.

UNITED STATES PATENT AND TRADEMARK OFFICE
CERTIFICATE OF CORRECTION

PATENT NO.    : 4,656,301
DATED         : April 7, 1987
INVENTOR(S)   : Christian Prud ' Homme et al.

It is certified that error appears in the above-identified patent and that said Letters Patent is hereby corrected as shown below:

<u>Column 8,</u>
Line 5, through line 7, please delete "at least one of the alkali metals lithium, sodium, potassium and rubidium, or compound thereof", and insert therefore -- cesium metal or cesium compound --;
Line 14, please delete "alkali metal salts", and insert therefore -- cesium compound --;
Line 15, before "The", please insert -- The catalyst composition as defined by Claim 21, up to 90% by weight (calculated as cesium metal) of the cesium or cesium compound being replaced by at least one of the alkali metals lithium, sodium, potassium and rubidium, or by a compound of such alkali metals.

25. --

Line 17, please delete "25", and insert therefore -- 26 --;
Line 19, please delete "26", and insert therefore -- 27 --;
Line 22, please delete "27", and insert therefore -- 28 --; delete "26" and insert therefore -- 27 --;
Line 26, please delete "28"; and insert therefore -- 29 --.

This certificate supersedes Certificate of Correction issued November 5, 2002

Signed and Sealed this

Twenty-first Day of January, 2003

JAMES E. ROGAN
*Director of the United States Patent and Trademark Office*